(12) United States Patent
Coignet

(10) Patent No.: US 7,479,370 B2
(45) Date of Patent: Jan. 20, 2009

(54) DETECTION OF 13Q14 CHROMOSOMAL ALTERATIONS

(75) Inventor: Lionel J. Coignet, Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/937,514

(22) Filed: Sep. 8, 2004

(65) Prior Publication Data

US 2005/0079531 A1    Apr. 14, 2005

Related U.S. Application Data

(60) Provisional application No. 60/501,070, filed on Sep. 8, 2003.

(51) Int. Cl.
- C12Q 1/68 (2006.01)
- C12P 19/34 (2006.01)
- C07H 21/02 (2006.01)
- C07H 21/04 (2006.01)

(52) U.S. Cl. .................. 435/6; 435/91.1; 435/91.2

(58) Field of Classification Search .................. None
See application file for complete search history.

(56) References Cited

OTHER PUBLICATIONS

Shaughnessy et al; Blood, vol. 15, pp. 1505-1511; 2000.*
Konigsberg et al; Leukemia, vol. 14, pp. 1975-1979, 2000.*
Bullrich et al; Blood, vol. 88, pp. 3109-3115; 1996.*
Zech et al; Hereditas, vol. 108, pp. 77-84, 1988.*
Hawthorn et al; Genomics, vol. 30, pp. 425-430, 1995.*
GenBank Accession No. AL136525 (Apr. 2001).*
GenBank Accession No. AL136527 (Apr. 2000).*
Döhner, et al., *Chromosome aberrations in B-cell chronic lymphocytic leukemia: reassessment based on molecular cytogenetic analysis*, J Mol Med, 1999, V.77, pp. 266-281.
Bullrich, et al., *Minimal Region of Loss at 13q14 in B-Cell Chronic Lymphycytic Leukemia*, Blood, Oct. 15, 1996, V. 88, No. 8, pp. 3109-3115.
Migliazza, et al., *Necleotide sequence, transcription map, and mutation analysis of the 13q14 chromosomal region deleted in B-cell chronic lymphocytic leukemia*, Blood, Apr. 1, 2001, V. 97, No. 7, pp. 2098-2104.
Bullrich, et al., *Characterization of the 13q14 Tumor Suppressor Locus in CLL: Identification of ALT1, an Alternative Splice Variant of the LEU2 Gene*, Cancer Research, Sep. 15, 2001, V. 61, pp. 6640-6648.
Cuneo, et al., *Cytogenetic Profile of Lymphoma of Follicle Mantle Lineage: Correlation with Clinicobiologic Features*, Blood, Feb. 15, 1999, V. 93, No. 4, pp. 1372-1380.
Shaughnessy, Jr., et al., *High incidence of chromosome 13 deletion in multiple myeloma detected by multiprobe interphase FISH*, Blood, Aug. 15, 2000, V. 96, No. 4, pp. 1505-1511.
Zojer, et al., *Deletion of 13q14 remains an independent adverse prognostic variable in multiple myeloma despite its frequent detection by interphase fluorescence in situ hybridization*, Blood, Mar. 15, 2000, V. 95, No. 6, pp. 1925-1930.
Meyer, et al., *Establishment of the B cell precursor acute lymphoblastic leukemia cell line MUTZ-5 carrying a (12;13) translocation*, Leukemia, 2001, V. 15, pp. 1471-1474.
Chapman, et al., *Frequent homozygous deletions of the D13S25 locus in chromosome region 13q14 defines the location of a gene critical in leukaemogenesis in chronic B-cell lymphocytic leukaemia*, Oncogene, 1994, V. 9, pp. 1289-1293.
Bouyge-Moreau, et al., *Construction of a 780-kb PAC, BAC, and Cosmid Contig Encompassing the Minimal Critical Deletion Involved in B Cell Chronic Lymphocytic Leukemia at 13q14.3*, Genomics, 1997, V. 46, Article No. GE975008, pp. 183-190.
Kalachikov, et al., *Cloning and Gene Mapping of the Chromosome 13q14 Region Deleted in Chronic Lymphocytic Leukemia*, Genomics, 1997, V. 42, Article No. GE974747, pp. 369-377.
Heerema, et al.; Abnormalities of Chromosome Bands 13q12 to 13q14 in Childhood Acute Lymphoblastic Leukemia; Journal of Clinical Oncology, vol. 18, No. 22, Nov. 15, 2000; pp. 3837-3844; XP-002416967.
Cave, et al.; Deletion of chromosomal region 13q14.3 in childhood acute lymphoblastic leukemia; Leukemia (Basingstoke), vol. 15, No. 3, Mar. 2001; pp. 371-376; XP-002416968.
Coignet, et al.; Myeloid- and Lymphoid-Specific Breakpoint Cluster Regions in Chromosome Band 13q14 in Acute Leukemia; Genes, Chromosomes & Cancer, vol. 25, No. 3, Jul. 1999; pp. 222-229; XP-002416969.
Kitamura, et al.; A transcription map of the minimally deleted region from 13q14 in B-cell chronic lymphocytic leukemia as defined by large scale sequencing of the 650 kb critical region; Onogene, vol. 19, No. 50, Nov. 23, 2000; pp. 5772-5780; XP-002416970.
Calin, et al.; Frequent deletions and down-regulation of micro-RNA genes miR15 and miR16 at 13q14 in chronic lymphocytic leukemia; Proceedings of the National Academy of Sciences of USA, National Academy of Science, Washington, D.C., vol. 99, No. 24, Nov. 26, 2002; pp. 15524-15529; XP-002982123.
Mabuchi, et al.; Cloning and Characterization of CLLD6, CLLD7, and CLLD8, Novel Candidate Genes for Leukemogenesis at Chromosome 13q14, a Region Commonly Deleted in B-Cell Chronic Lymphocytic Leukemia; Cancer Research, American Associate for Cancer Research, Baltimore, MD, vol. 61, No. 7, Apr. 1, 2001; pp. 2870-2877; XP-002233928.
Coignet, et al.; Molecular Characterization of a t(12;13) (p12;q14) Translocation in Pre-B ALL, Resulting in the Silencing of ETV6 and a New Gene, SDRALL, at 13q14; Blood, vol. 100, No. 11, Nov. 16, 2002; 1 page; Abstract No. 4252; XP-009077664.
Database EMBL [Online]; *Homo sapiens* WD40- and FYVE-domain containing protein 2, WDF2 mRNA, complete cds; Retrieved from NCBI accession No. AF411978; 1 page; XP-002416975.

* cited by examiner

*Primary Examiner*—Jehanne S Sitton
(74) *Attorney, Agent, or Firm*—Hodgson Russ LLP

(57) ABSTRACT

The present invention relates to methods for detection of chromosomal alterations which are associated with the presence of various leukemias and lymphomas. The method comprises the steps of obtaining a biological sample comprising lymphocytes from an individual and assaying the sample to detect chromosomal deletions in the regions of chromosome 13 that corresponds to the region of chromosome 13 present in the RP11-147H23 or RP11-327P2.

5 Claims, 3 Drawing Sheets

Panel 1

Panel 2

Panel 3

DETECTION OF 13Q14 CHROMOSOMAL ALTERATIONS

This application claims priority of U.S. Provisional Application Ser. No. 60/501,070 filed on Sep. 8, 2003, the disclosure of which is incorporated herein by reference.

FIELD OF THE INVENTION

The present invention relates generally to the field of lymphoproliferative diseases and more particularly to a method for detecting chromosomal alterations associated with such diseases.

BACKGROUND OF THE INVENTION

B-cell chronic lymphocytic leukemia (B-CLL), represents the most common leukemia in Western countries and has an estimated incidence of 1 per 100,000 per year. It is characterized by the monoclonal expansion of B lymphocytes expressing the CD5 marker and exhibiting a long life span, possibly because of a perturbed apoptotic program.

Current knowledge of the molecular pathogenesis of B-CLL is limited because no specific genetic alteration has yet been associated with this disease. In particular, B-CLL is not associated with reciprocal balanced chromosomal translocations. Accordingly, none of the proto-oncogenes involved in chromosomal translocations in other mature B cell malignancies, including cyclin D1, BCL-2, BCL-6, PAX-5, and c-MYC, are primarily altered in B-CLL. Although in a fraction of B-CLL cases inactivation of the tumor suppressor gene p53 (on chromosome 17p13) and deletions or mutations of the ATM gene (on chromosome 11q22-23) have been reported, such lesions were observed in late stages of the disease and may not represent primary tumorigenic events. However, it is known that at the chromosomal level the 13q14 region of human chromosome 13 is very frequently deleted in several hematological malignancies. Chromosome 13q14 deletions (approximately 50% of the patients) are the most common chromosomal alterations associated with B-CLL (Dohner et al, J Mol Med.;77:266-281. 1999; Kalachikov et al, Genomics.;42:369-377. 1997), followed by structural aberrations of chromosome 11q (19% of the cases) and trisomy of chromosome 12 (15%). Moreover, chromosome 13 deletions can be the only cytogenetically detectable abnormality, suggesting an early role in B-CLL pathogenesis. Similarly, 13q14 alterations, mainly deletions, are frequently observed in acute leukemia, multiple myeloma and mantle cell lymphoma. Alterations of 13q14 (25-40% of samples) provide myeloma patients with a statistically significant adverse prognostic as an independent factor of outcome (Zojer et al, Blood 2000 95:1925-30; Shaughnessy et al, Blood 2000 96:1505-11). It has also been shown that deletion of chromosome 13 is associated with transition from monoclonal gammopathy of undetermined significance (MGUS) to multiple myeloma. Deletion of 13q14 has been also observed in 50% of mantle cell lymphoma cases (Cuneo et al, Blood 1999 93:1372-80).

The karyotyping of CLL samples identified relatively few chromosomal abnormalities, suggesting that the specificity and frequency of observed deletions at 13q14 have pathologic significance. Several groups have used positional cloning to identify the gene or genes targeted by the deletions. A region of more than 1 Mb has been fully sequenced and characterized in detail (Bullrich et al, Cancer Res 2001 61:6640-8; Migliazza et al, Blood 2001 97:2098-2104). So far, a total of eight genes have been identified and screened for alterations at the DNA and/or RNA level in sporadic and familial cases of CLL: Leu-1 (BCMS or EST70/Leu-1), Leu 2 (ALT1 or 1B4/Leu-2), Leu 5 (CAR), CLLD6, KPNA3, CLLD7, LOC51131 (putative zinc finger protein NY-REN-34 antigen) and CLLD8. However, detailed genetic analysis, including extensive loss of heterozygosity (LOH), mutation, and expression studies, have failed to demonstrate the consistent involvement of any of the genes located in the deleted region.

With the definition of a minimally deleted region in 13q14.3 between markers D13S31 and RB1 it became possible to analyze larger numbers of tumors for loss of heterozygosity (LOH) status where it was soon shown that homozygous deletions were largely centered around the D13S25 locus (Chapman et al, Oncogene 1994 9:1289-93). The observation of homozygous deletions also demonstrated that it is the loss of function of a critical gene in 13q14 which is important in the development of B-CLL. Subsequent analyses of larger numbers of tumors confirmed the observation of homozygous deletions and enabled a refinement of the limits of the minimally deleted region (Bullrich et al, Blood 1996, 88: 3109-15; Bouyge-Moreau et al, Genomics 1997, 46:183-90).

Although there is some variation between reports attempting to define ever decreasing sizes of the critical region, these often depended on the observation in single tumors which might have been due to peculiar rearrangements in these cases, possibly unrelated to leukemogenesis. At present, the critical region is understood to be in a region approximately 700 kb and bounded by markers D13S319 and D13S25.

Accordingly, large screenings were undertaken using different approaches, of which FISH was one of the most prominent, using genomic probes specific for the markers RB1, D13S25 and D13S319 (commercially available now from companies like Vysis, Inc.). However, none of the genes and/or probes used in these screenings achieved a 100% detection rate of 13q14 deletions in CLL. The same region/genes of 13q14 were studied in multiple myeloma and mantle cell lymphoma but no consistent observations have been made for a potential tumor suppressor gene located at 13q14.

Subsequently, a project for the characterization of 13q breakpoints in acute leukemia was initiated which utilized a cell line from one of the patient samples harboring a unique t(12;13)(p12;q14) translocation (Meyer et al, Leukemia 2001 15(9): 1471-4). This cell line has been used to identify the gene(s) involved in this rearrangement to establish a molecular characterization of the pathogenetic events potentially leading to leukemia. One of the pathologic consequences of such a translocation is the creation of tumor-specific fusion genes from the juxtaposition of segments of DNA normally found on separate chromosomes. Recurrent chromosomal deletions, on the other hand, suggest the presence of a tumor suppressor gene within the deleted region, deletion of one allele being associated with mutation of the other. While the gene involved in this single translocation on chromosome 12p12 was identified as the ETV6 gene which has been involved in many balanced translocations, attempts to clone a potential partner gene were unsuccessful.

Thus, there is a need for a method of detecting chromosomal alterations in the 13q14 region of human chromosome 13 which indicate an individual is likely to have acute lymphoblastic leukemia (ALL) or chronic lymphocytic leukemia (CLL).

SUMMARY OF THE INVENTION

The present invention provides a method for determining whether an individual is likely to have ALL or CLL. The method comprises the steps of obtaining a sample of cells from the blood or bone marrow comprising lymphocytes of the individual and detecting if a portion of the 13q14 region of chromosome 13, whose sequence corresponds to the sequence of chromosome 13 within the bacterial artificial chromosomes (BAC) RP11-147H23 or RP11-327P2 is deleted.

In one embodiment, the step of detecting if a portion of the 13q14 region of chromosome 13 in a cell from the individual is deleted comprises performing fluorescent in situ hybridization (FISH) assays of the chromosomes of the individual. In one aspect of this method, FISH assays are performed to determine the hybridization patterns of a test probe and a control probe, wherein the test probe corresponds to a sequence within BAC RP11-147H23 or RP11-327P2 and the control probe corresponds to a sequence on chromosome 13 outside the regions within BAC RP11-147H23 and RP11-327P2. A hybridization pattern wherein two pairs of co-localized signals from the test and control probes means there is no deletion, and only one pair of co-localized signals is indicative of the presence of a deletion.

In another embodiment, the step of detecting if a portion of the 13q14 region of chromosome 13 is deleted comprises performing FISH analysis of the region of chromosome 13 comprising the WDFY2 gene to determine whether there are two complete copies of the WDFY2 gene in a cell. In one aspect of this method, hybridization patterns of a first and second probe are determined, wherein the first probe corresponds to a first exon of the WDFY2 gene and the second probe corresponds to a second exon of the WDFY2 gene. A hybridization pattern wherein there is only one pair of co-localized signals detected is indicative of the presence of a single complete copy of the WDFY2 gene in the cell.

In another embodiment, the step of assaying the nucleic acids comprises detection of the presence of mRNA transcribed from genes located in the region of chromosome 13 corresponding to BAC RP11-147H23. In a particular embodiment of this method, RT-PCR is performed to detect the presence or absence of mRNA expressed from the WDFY2 gene.

DETAILED DESCRIPTION OF THE INVENTION

Figure 1:
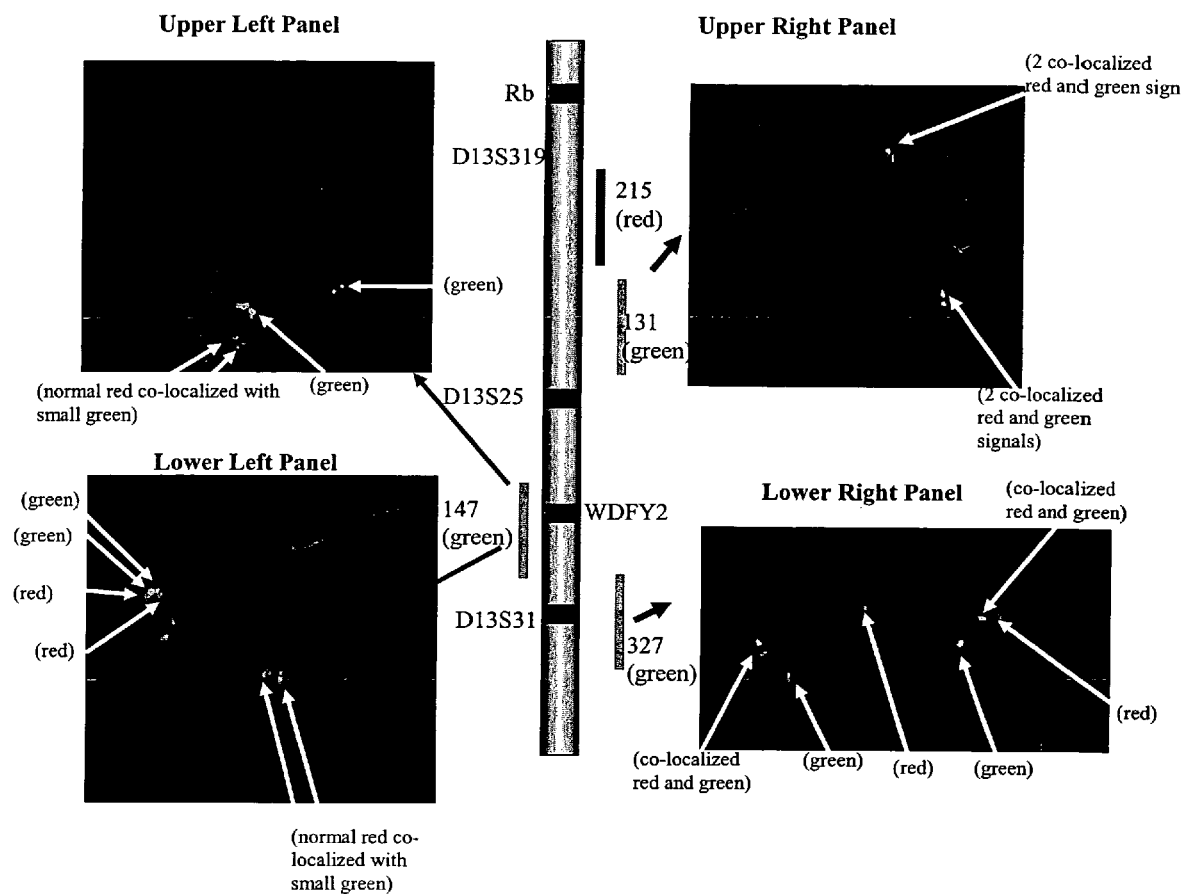
FIG. 1 is a photographic representation of a FISH analysis of MUTZ5 cells (upper land lower left panels), cells taken from individuals diagnosed with CLL (lower right panel) and a cell taken from a normal individual (upper right panel). By chromosome walking using BAC clones 215, 131, 147 and 327, BAC clone 147 was identified as spanning the 13q14 breakpoint.

The present invention provides a method for determining whether an individual is likely to be diagnosed as having ALL or CLL. The method comprises the steps of obtaining a sample of cells from the blood or bone marrow of the individual, wherein the sample comprises lymphocytes, and detecting whether a portion of the 13q14 region of chromosome 13 is deleted. The portion of 13q14 that is analyzed for deletion lies between the D13S25 and D13S31 markers and corresponds to the region of chromosome 13 that is present in the bacterial artificial chromosome (BAC) RP11-147H23 or RP11-327P2. Detection of a deletion in this region is indicative of a likelihood that the individual has CLL or ALL.

The lymphocytes analyzed in the method of the present invention can be obtained by any method. For example, the lymphocytes can be present in blood collected using standard phlebotomy techniques. Bone marrow comprising lymphocytes can be obtained by aspiration or biopsy using a needle inserted into the bone.

Nucleic acids in the lymphocytes can be assayed by a variety of methods for detecting chromosomal deletions, such as northern blots, Southern blots, restriction fragment length polymorphism analysis, the polymerase chain reaction (PCR), reverse transcriptase PCR (RT-PCR), rapid amplification of cDNA ends (RACE), FISH assays, or any method known to those skilled in the art for nucleic acid detection.

In one embodiment, FISH is used to determine whether an individual is likely to be diagnosed as having ALL or CLL. FISH is a cytogenetic technique used to identify the presence or absence of chromosomes or chromosomal regions by hybridization of fluorescently-labeled DNA (a probe) to denatured chromosomal DNA. FISH can be performed in any manner known to those skilled in the art, but FISH procedures performed by many laboratories around the world are generally similar to those of Kuo, et al., ("Detection of Aneuploidy Involving Chromosomes 13, 18 or 21, by Fluorescence in Situ Hybridization to Interphase and Metaphase Amniocytes," Am. J. Hum. Genet. 49:112-119 (1991)); Klinger, et al., ("Rapid Detection of Chromosome Aneuploidies in Uncultured Amniocytes by Using Fluorescence in Situ Hybridization (FISH)," Am J. Hum. Genet. 51:55-65 (1992)); and Ward, B. E., et al., ("Rapid Prenatal Diagnosis of Chromosomal Aneuploidies by Fluorescence in Situ Hybridization; Clinical Experience with 4,500 Specimens," Am. J. Hum. Genet. 52:854-865 (1993)).

In general, performing a FISH analysis comprises the steps of obtaining a biological sample containing chromosomal DNA, denaturing the DNA, hybridizing fluorescently-labeled DNA to the denatured chromosomal DNA and using fluorescent microscopy to obtain a hybridization pattern. Methods for obtaining fluorescently labeled probes for use in FISH analysis are well known in the art, such as by labeling the DNA probe by nick translation with fluorochrome-conjugated nucleotides. This can be achieved using commercially available kits (Vysis, Downers Grove, Ill.). Examples of suitable fluorochrome-conjugated nucleotides include FITC-labeled nucleotides which fluoresce in green, Texas Red-conjugated nucleotides which fluoresce in red, and the like.

In one embodiment, the FISH assays can be performed using polynucleotides as probes wherein the polynucleotides comprise portions of human chromosome 13q14 region on human chromosome 13. Such polynucleotides may be provided in a variety of forms, including as portions of cosmids, yeast artificial chromosomes or bacterial artificial chromosomes (BACs).

In one embodiment, FISH is used to determine whether an individual is likely to have CLL or ALL by detecting the relative locations of a control probe and a test probe to determine whether there has been a deletion in the 13q14 region of chromosome 13. In a particular aspect, the region of chromosome 13 analyzed for deletion is the region of chromosome 13 that corresponds to BAC RP11-147H23 or RP11-327P2.

In one embodiment of such a method, a FISH assay using a test polynucleotide probe that comprises a region of chromosome 13 which corresponds to the sequence of BAC RP11-147H23 can be used in combination with a control probe that hybridizes to chromosome 13 outside the region of chromosome 13 which corresponds to the sequence of BAC RP11-147H23. Each probe can be labeled with fluorochrome-conjugated nucleotides that fluoresce in different colors such that the probes can be distinguished from one another.

Hybridization of this pair of probes to a normal chromosome 13 produces a predictable hybridization pattern such that the signals from each pair of probes is co-localized on a single chromosome 13 chromatid. This result is produced on each chromatid of the two homologous chromosome 13's in the cell. (After S-phase, there are two binding sites for each probe on each chromosome due to the replicated chromatids being joined at the centromeres.)

In contrast, a similar FISH assay performed on a cell comprising a deletion in a region of the chromosome corresponding to the BAC RP11-147H23 sequence will produce a different hybridization pattern. In this case, one pair of probes may be co-localized on the normal chromosome 13, but the pair of probes on the: homologous chromosome comprising the deletion will not be co-localized. Rather, the signal from the test probe may be separated onto distinct chromosomes due to the region of the chromosome corresponding to the BAC RP11-147H23 sequence having been translocated. In the case of complete deletion of the region of the chromosome corresponding to the BAC RP11-147H23, the signal from the test probe is not detected at all. Such hybridization patterns indicate the individual from whom the chromosome was obtained is likely to be diagnosed with CLL or ALL.

In another embodiment, when a FISH assay is performed on a cell comprising a deletion in a region of the chromosome corresponding to the BAC RP11-147H23, the test probe and control probes may be on opposite sides of the deletion. In this embodiment, when a normal chromosome 13 and a chromosome 13 with a deletion in the region of the chromosome corresponding to BAC RP11-147H23 are present, the test probe and the control probe will be co-localized on the normal chromosome 13, but not co-localized on the chromosome comprising the deletion. The signal from 327 also will not be split because the 327 clone does not span the chromosomal breakpoint.

In another embodiment, a panel of probes corresponding to portions of the region of the chromosome corresponding to the region of chromosome 13 present in BAC RP11-147H23 may be used in FISH assays. This aspect of the invention can be used to determine whether there are two complete copies of the WDFY2 gene (GenBank WDFY2 cDNA accession number is NM052950; in a cell. In an embodiment of this method, FISH hybridization patterns of first and second fluorescently labeled probes are determined, wherein the first probe corresponds to a first exon of the WDFY2 gene and the second probe corresponds to a second exon of the WDFY2 gene. A hybridization pattern wherein there is only one pair of co-localized signals detected is indicative of the presence of only one complete copy of the WDFY2 gene in the cell.

In another embodiment of the present invention, nucleic acids can be isolated from the cells in the sample and analyzed by methods such as northern blots, Southern blots, restriction fragment length polymorphism analysis, the polymerase chain reaction (PCR), reverse transcriptase PCR (RT-PCR), rapid amplification of cDNA ends (RACE) or any method known to those skilled in the art for nucleic acid detection to determine if an individual is likely to have ALL or CLL as evidenced by a deletion in the region of chromosome 13 corresponding to the BAC RP11-147H23 or RP11-327P2 sequence.

By way of illustration, the nucleic acids, typically DNA in the case of a PCR analysis or total mRNA for a RT-PCR analysis, are extracted from the lymphocytes in blood cells or bone marrow. Both DNA and RNA can be extracted according to routine procedures well known in the art. For examples see Maniatis, T., et al., "Molecular Cloning—A Laboratory Manual", Cold Spring Harbor Laboratory (1982). PCR reactions can be performed in a variety of ways known to those skilled in the art. Similarly, once mRNA is isolated it can be subjected to RT-PCR. Generally, RT-PCR comprises the steps of reverse transcribing mRNA into cDNA, and subsequently amplifying reverse-transcribed cDNA by polymerase chain reaction.

According to an embodiment of the present invention, for an RT-PCR reaction, any primers that can amplify mRNA transcribed from the region of DNA corresponding to the sequence of the BAC RP11-147H23 clone may be used to detect the presence or absence such mRNA, wherein the absence of such mRNA in indicative that the individual from whom the total mRNA was obtained is likely to be diagnosed with ALL or CLL.

In a particular embodiment, RT-PCR is used to detect cDNA from the WDFY2 gene. As disclosed herein, BAC RP11-147H23 comprises the WDFY2 gene which spans a chromosomal breakpoint such that, when chromosomal deletions in this span are present, the individual from which the chromosome was obtained is likely to be diagnosed as having ALL or CLL.

Both PCR and RT-PCR reaction products can be analyzed by methods known in the art, including but not limited to gel electrophoresis, DNA sequencing and the like. Amplification of nucleic acid sequences normally located in the region of chromosome 13 corresponding to the BAC RP11-147H23 or RP11-327P2 sequence indicates a lack of chromosomal deletion, while the absence of such amplification is evidence of deletion in the region. Such deletions are shown herein to be indicative that the individual from whom the sample analyzed by RT-PCR is taken is likely to have CLL.

In yet another embodiment of the invention, kits for detecting chromosomal deletions in the region of chromosome 13 corresponding to the region of chromosome 13 present in BAC RP11-147H23 or RP11-327P2 are provided.

The present invention is illustrated by the following Examples which are not meant to be limiting in any way.

EXAMPLE 1

The present Example provides an illustration whereby a DNA sequence for use in determining that an individual is likely to have ALL or CLL can be identified.

In order to identify such a sequence, a FISH chromosomal walking approach on human chromosome 13 was undertaken using RPCI BAC clones RP11-147H23, RP11-215B15 (GenBank accession no. AL136527), RP11-131F1 (AL157761) and RP11-327P2 (AL 162377) also referred to herein as "147", "215", "131" and "327," respectively.

To prepare the BAC clones for use in FISH assays, the BAC DNAs were extracted from $E.$ $coli$ using a DNA extraction kit (Qiagen). The extracted BAC DNA was then subject to nick translation labeling with fluorochrome-conjugated nucleotides using a commercially available kit (Vysis, Downers Grove, Ill.).

These clones were utilized in a double color FISH assay. In this approach, the 215 clone was used in combination with each of the three remaining BAC clones in individual FISH assays. The 215 clone is emits a red fluorescent signal and serves as a reference point on chromosome 13, meaning the location of a red fluorescent signal corresponds to the physical location of chromosome 13 in the FISH assay result. The other BAC clones emit a green fluorescent signal.

Shown in FIG. 1 are FISH assays in a MUTZ5 cell line which is known to have a translocation of chromosome 13 in the 13Q14 region (upper and lower left panels), cells taken from a normal individual (upper right panel) and cells taken from a CLL patient (lower right panel). The chromatid depicted in the center of the four panels includes a map of the relative positions of the Rb locus, the D13S319 marker, the D13S25 marker, the WDFY2 gene, and the D13S31 locus in the downstream orientation, respectively. The red vertical bar represents the hybridization location of the 215 clone (the control probe), while the green vertical bars represent the hybridization locations of the remaining three BAC clones (test probes) which are designated by their three digit abbreviations. The arrows demonstrate which BAC clones were used to produce the hybridization patterns in each of the four panels. The 215 clone was used in each panel.

As can be seen from FIG. 1, upper right panel, hybridization of clones 215 and 131 resulted in co-localized signals. (There are two sets of signals because of hybridization of the clones to each of the chromatids of the two chromosome 13 homologues.) This result demonstrates that the chromosomal loci to which these clones hybridize lay outside the location where the chromosome breaks during translocation, as neither the red or green signal is absent or translocated to a different chromosome (i.e., not co-localized).

Hybridization of clones 215 and 327 as shown in the lower right hand panel of FIG. 1 (which depicts two cells taken from a patient with CLL) results in a hybridization pattern wherein one green and one red signal are co-localized on the "normal" chromosome 13 homologue, and the other pair of red and green signals is split apart. This result indicates that the chromosomal breakpoint was localized between the hybridization site of the 215 and 327 clones, because for one pair of probes, the entire detected green signal is separated from the red signal, indicating the portion of the chromosome comprising sequence complementary to the 327 probe was translocated away from the region of the chromosome to which the 215 clone hybridizes.

In the left upper and lower panels of FIG. 1, hybridization of clones 215 and 147 result in a hybridization pattern wherein one green and one red signal are co-localized. However, in the other pair of red and green signals, a normal red signal was co-localized with a small green signal. This hybridization pattern is due to a translocation of a portion of the chromosome to which a portion of the 147 clone binds. Further, an additional small green signal can be seen on the derivative (translocation partner) chromosome 12, which indicates the location of the translocated portion of chromosome 13.

Therefore, this Example demonstrate the identification of a chromosomal breakpoint in CLL cells, that clone 147 spans the chromosomal breakpoint which contains the sequences/gene(s) that are involved in the translocation, and that the region of chromosome 13 corresponding to the sequence of chromosome 13 present in RP11-327P2 is downstream of the breakpoint.

EXAMPLE 2

This Example demonstrates that the double color FISH assay described in Example 1 is useful for determining that an individual is likely to have ALL.

A series of bone marrow samples from 9 individuals diagnosed with ALL were analyzed with the RP11-147H23 clone in combination with the RP11-215B13 (clone 215 from Example 1). These probes were hybridized as described and detected as described in Example 1. Eight out of nine samples showed a deletion of one allele, as summarized in Table 1.

TABLE 1

| Pt No | 13q abnormality | % del (BAC 147) | Control Probe |
| --- | --- | --- | --- |
| 1948 | del(13)(q12q14) | 22 | + |
| 1217 | del(13)(q12q22) | 67 | − |
| 1539 | del(13)(q14q22) | 92 | + |
| 2280 | del(13)(q13) | 37 | − |
| 2040 | del(13)(q14q32) | 90 | + |
| 1454 | del(13)(q14q22) | 0 | + |
| 2747 | del(13)(q12q22) | 90 | − |
| 1001 | del(13)(q14q21) | 50 | − |
| 1037 | der(9)t(9; 13)(p21; q14) | 30 (del/split) | + |

The patients showing (−) for the control probe were interpreted as having a chromosomal deletion that encompassed the region of the chromosome to which the control probe is complementary.

Therefore, this Example demonstrate that clone 147 can be used to detect a deletion in the region of chromosome 13 in individuals diagnosed with ALL.

EXAMPLE 3

This Example demonstrates that the double color FISH assay described in Example 1 is useful for determining that an individual is likely to have CLL.

Figure 2:
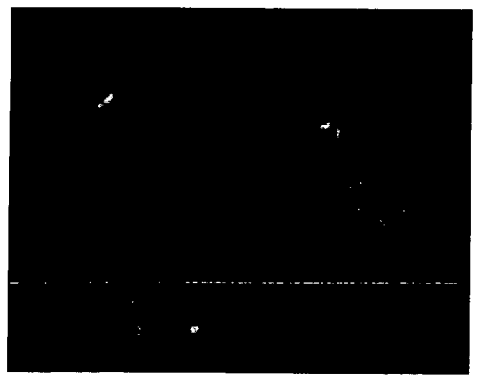
FIG. 2 is a photographic representation of a FISH analysis of CLL patient samples showing FISH hybridization patterns demonstrating deletion of the region of chromosome 13 corresponding to the sequence of the BAC clone 147 in 10 samples divided into panels 1-3.
Figure 2:
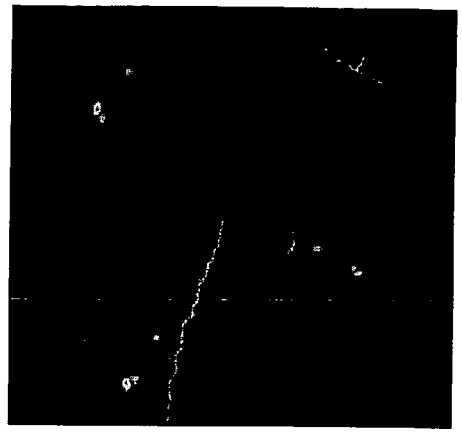
Figure 2:
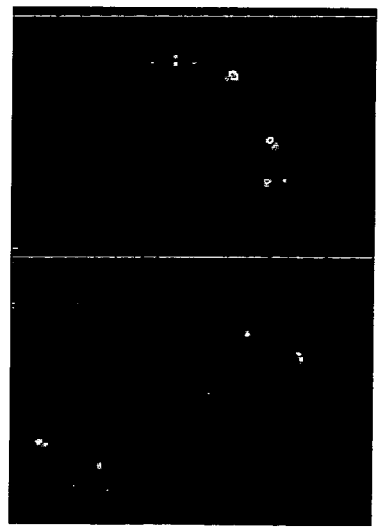

To investigate chromosomes from individuals afflicted with CLL, ten CLL cases were randomly selected for FISH analysis. As can be seen in the three panels of FIG. 2, all 10 assays (shown distributed in panels 1-3 of FIG. 2) showed a deleted FISH hybridization pattern as demonstrated in each case by the pair of co-localized red and green signals and the unpaired red signal from a chromosome 13 in which the region to which the 147 clone would normally hybridize is deleted. An additional 25 CLL cases from Roswell Park Cancer Institutes (RPCI) were studied using this technique and 18/21 (85%) of these showed a deleted hybridization pattern (data not shown).

Further, a series of non selected samples were hybridized also analyzed by FISH with the 147 and 215 clones. The results summarized in Table 2 represent the % of cells presenting a deleted hybridization pattern for clone 147.

TABLE 2

FISH study on non-selected CLL patient samples.

| Patient # | Diagnosis | % of cells with 13q14 del |
|---|---|---|
| C1 | Control | 6 |
| C2 | Control | 7.5 |
| C3 | Control | 8 |
| 1 | CLL | 34 |
| 2 | CLL | 22 |
| 3 | CLL | 47 |
| 4 | CLL | 66 |
| 5 | CLL | 15 |
| 6 | CLL | 23 |
| 7 | CLL | 21 |
| 8 | CLL | 30 |
| 9 | CLL | 27 |
| 10 | CLL | 29 |
| 11 | CLL | 65 |
| 12 | Atyppical CLL | 8 |
| 13 | CLL | 26 |
| 14 | CLL | 20 |
| 15 | CLL | 18 |
| 16 | CLL | 13 |
| 17 | CLL | 14 |
| 18 | CLL | 33 |
| 19 | CLL | 23 |
| 20 | CLL | 15 |
| 21 | CLL | 19 |
| 22 | CLL | 12 |
| 23 | CLL | 17 |
| 24 | CLL | 21 |
| 25 | CLL | 85 |
| 26 | CLL | 68 |
| 27 | CLL | 27 |
| 28 | CLL | 15 |
| 29 | CLL | 9 |
| 30 | CLL | 7 |
| 31 | CLL | 18 |
| 32 | CLL | 22 |

Table 2 demonstrates that individuals afflicted with CLL have cells with hybridization patterns characteristic of a deletion of the region of chromosome 13 corresponding to the region of human chromosome 13 within the 147 clone. While normal individuals (i.e., the controls designated C1-C3) also show a percentage of cells with in which hybridization patterns characteristic of a deletion of this can be detected, it will be clear to one skilled in the art that such percentages can be used to establish background deletion detection levels from which a threshold of cell percentages indicative of the likelihood that an individual from whom the cells were obtained will be diagnosed with CLL.

EXAMPLE 4

This Example illustrates the detection of chromosome 13 deletions in samples from individuals with CLL with respect to the expression (or lack thereof) of a gene located within the region of chromosome 13 corresponding to the 147 clone.

Twelve DNA samples from CLL cases were analyzed by RT-PCR for expression of the WDFY2 gene. The primers used in the RT-PCR reaction amplify the whole open reading frame for WDFY2. The forward primer has the sequence: 5' tctgtctcaacctgtgtccc 3' (SEQ ID NO:1) and the reverse has the sequence 5' gaagagtccccttgcgagt 3' (SED ID NO:2).

Figure 3:
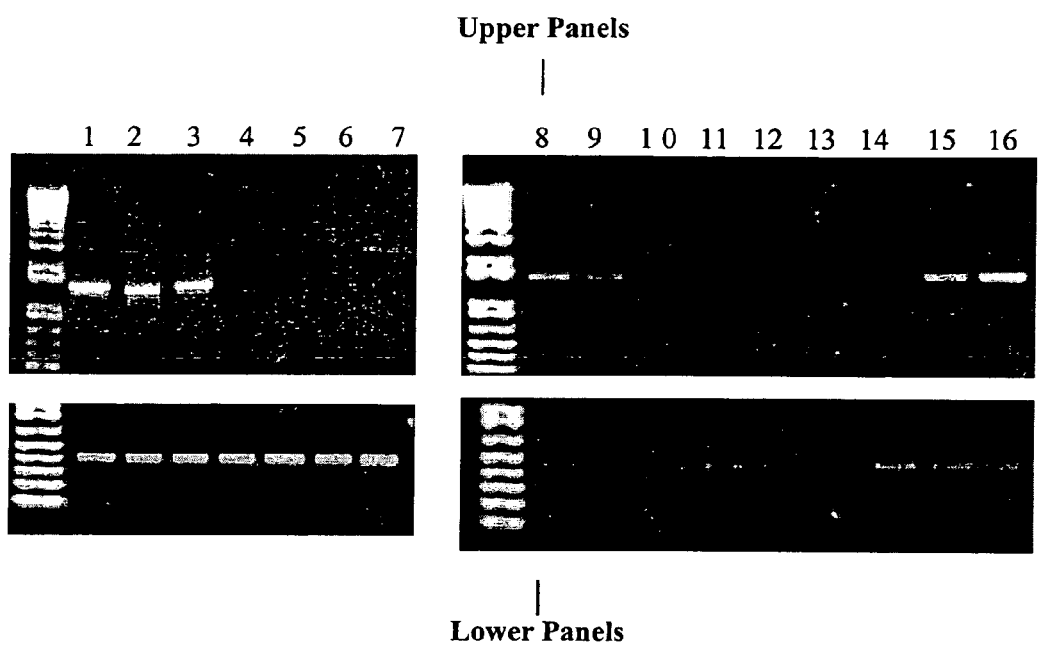
FIG. 3 is a photographic representation of a gel after electrophoretic separation of RT-PCR amplification products of WDF2 and control cDNAs. The upper panels represent amplification of WDF2 cDNA using RT-PCR. The lower panel represents RT-PCR of the GAPDH amplification for loading controls. The lanes represent separation of RT-PCR amplification products from various sources as follows: Lane 1: EBV-LIN (immortalized lymphocytes); Lane 2: G519 (Mantle cell lymphoma); Lane 3: normal lymphocytes; Lanes 4-15: CLL samples; Lane 16: EBV-LIN. The two unlabeled lanes are size markers.

FIG. 3 depicts a photograph of a gel after electrophoretic separation of RT-PCR amplification products. The lower panel represents RT-PCR of the GAPDH amplification used as loading controls. Shown in lanes 1 and 16 are assays of EBV-LIN cells (immortalized lymphocytes) and twelve CLL samples (lanes 4-7 and 8-15). Four CLL samples (lanes 4-7) were negative for WDF2 mRNA, indicating either a deletion of the WDF2 gene or chromosomal elements required for its expression. An additional eight samples were analyzed using the same approach (lanes 8-14) and showed heavily down-regulation of WDFY2 levels.

Detection of the heavily down-regulated expression of WDF2 mRNA in the samples of lanes 8-14 may be due to these samples not having been selected for high levels of CLL cells (the only selection criteria was active CLL), whereas the samples of lanes 4-7 were selected for high levels of CLL cells (i.e., by selecting individuals with about 95% CLL lymphocytes by fluorescence activated cell sorting.)

Thus, this Example demonstrates that detection of the absence of an mRNA encoded by the WDFY2 gene can be used to determine that the individual from whom the mRNA was isolated has a likelihood of being diagnosed with CLL.

EXAMPLE 5

This Example demonstrates that the detection of the absence of portions of the WDFY2 gene can be used to determine that an individual is likely to have CLL.

In order to acquire DNA probes specific for the WDFY2 gene, the WDFY2 cDNA was used as a probe to screen the LANL chromosome 13 specific cosmid library in a Southern blot. This library was obtained from the Human Genome Mapping Project (HGMP), Cambridge, UK) pre-gridded onto filters.

Six positive clones were identified from the Southern blot. The WDFY2 gene exons to which the clones mapped were identified by sequencing the 5' and 3' end of the clones and comparing the both ends with the WDFY2 gene sequence. Three of the clones were then labeled with fluorochrome-conjugated nucleotides that fluoresce in green, while three separate clones were labeled with fluorochrome-conjugated nucleotides that fluoresce in red.

TABLE 3

| Cosmid Name | Mapping/WDFY2 | Size (kb) | Color |
|---|---|---|---|
| 11I11 | Exon 1 | 33 | Green |
| 35P6 | Exon 2 | 47 | Green |
| 2N18 | Exon 2-3 | 39 | Green |
| 2N16 | Exon 4-6 | 40 | Red |

TABLE 3-continued

| Cosmid Name | Mapping/WDFY2 | Size (kb) | Color |
|---|---|---|---|
| 2K1 | Exon 6-12 | 38 | Red |
| 12L24 | Exon 10-12 + 3' seq | 45 | Red |

Fourteen CLL samples were studied using the FISH technique essentially as described in Example 1, with the exception that a cocktail comprising all six clones labeled as summarized in Table 3 were used as probes. The results from this FISH assay are summarized in Table 4.

TABLE 4

| Sample # | Normal FISH pattern (%) | Deleted FISH pattern (%) |
|---|---|---|
| Normal | 85 | 15 |
| 307 | 56 | 44* |
| 442 | 53 | 47* |
| 286 | 47 | 53* |
| 419 | 62 | 38* |
| 354 | 68 | 32* |
| 316 | 46 | 54* |
| 368 | 8 | 92* |
| 566 | 24 | 76* |
| 328 | 82 | 18 |
| 727 | 67 | 33* |
| 385 | 59 | 41* |
| 844 | 66 | 34* |
| 604 | 77 | 23 |
| 740 | 47 | 53* |

The numbers designated with an asterisk are based on a threshold percentage of cells that with detected deletions that are required to be considered an actual deletion. The threshold for detection of actual deletions from this experiment was set at 25%. Using this interpretation, 12/14 (86%) of the samples showed a deletion of the WDFY2 gene. The deletion in all cases summarized in Table 4 consisted of either one entire allele or the 5' end of the gene. Therefore, this Example demonstrates that detecting the absence of polynucleotides comprising regions of the WDFY2 gene can be used to determine whether there are two complete copies of WDFY2 in a cell, and thereby determine whether an individual is likely to be diagnosed as having CLL.

The foregoing description of the specific embodiments is for the purpose of illustration and is not to be construed as restrictive. From the teachings of the present invention, those skilled in the art will recognize that various modifications and changes may be made without departing from the spirit of the invention.

We claim:

1. A method of diagnosing an individual human as likely of having lymphoblastic leukemia (ALL) comprising the steps of:
   a) obtaining a sample of bone marrow or blood comprising lymphocytes from the individual, and
   b) detecting by fluorescence in situ hybridization (FISH) whether part of the 13q14 region of chromosome 13 present in bacterial artificial chromosome (BAC) RP11-147H23 is deleted in the lymphocytes, wherein the FISH analysis is performed using a test probe and a control probe, wherein the test probe is BAC RP11-147H23, and wherein the control probe is complementary to a sequence of chromosome 13 outside the region of chromosome 13 present in BAC RP11-147H23;
   wherein, in the FISH analysis, two pairs of co-localized signals from the test probe and control probe in the lymphocytes is indicative of the absence of a deletion, and wherein a split signal from the test probe and one pair of co-localized signals is indicative of the presence of a deletion;
   wherein a deletion detected in step b) is indicative of a likelihood of the individual as having ALL.

2. The method of claim 1, wherein the test probe and control probe are each labeled with a distinct fluorochrome-conjugated nucleotide.

3. The method of claim 1, wherein the control probe is either BAC RP11-215B15 or RP11-131F1.

4. A method of diagnosing a human—individual as likely of having CLL comprising the steps of:
  a) obtaining blood or bone marrow cells comprising lymphocytes from the individual;
  b) isolating mRNA from lymphocytes; and
  c) analyzing from b) WDFY2 mRNA expression,
  wherein absence of WDFY2 mRNA expression is indicative of the individual as likely of having CLL.

5. The method of claim 4, wherein analyzing WDFY2 mRNA expression is performed using RT-PCR, wherein—the RT-PCR is performed using a first primer consisting of the sequence of SEQ ID NO:1 and a second primer consisting of the sequence of SEQ ID NO:2.

* * * * *

```
                         SEQUENCE LISTING

<160> NUMBER OF SEQ ID NOS: 2

<210> SEQ ID NO 1
<211> LENGTH: 20
<212> TYPE: DNA
<213> ORGANISM: human chromosome 13

<400> SEQUENCE: 1
tctgtctcaa cctgtgtccc                                                 20

<210> SEQ ID NO 2
<211> LENGTH: 19
<212> TYPE: DNA
<213> ORGANISM: human chromosome 13

<400> SEQUENCE: 2
gaagagtccc cttgcgagt                                                  19
```